(12) United States Patent
King et al.

(10) Patent No.: US 12,097,359 B2
(45) Date of Patent: Sep. 24, 2024

(54) AGENT DELIVERY DEVICES

(71) Applicant: Boston Scientific Scimed, Inc., Maple Grove, MN (US)

(72) Inventors: Joseph King, Franklin, MA (US); Andrew Pic, Northboro, MA (US); John Favreau, Spencer, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 909 days.

(21) Appl. No.: 17/139,139

(22) Filed: Dec. 31, 2020

(65) Prior Publication Data
US 2021/0205541 A1 Jul. 8, 2021

Related U.S. Application Data (60) Provisional application No. 62/957,492, filed on Jan. 6, 2020.

(51) Int. Cl.
*A61M 5/315* (2006.01)
*A61B 1/015* (2006.01)
(Continued)

(52) U.S. Cl.
CPC ...... *A61M 5/3157* (2013.01); *A61M 5/14526* (2013.01); *A61M 31/00* (2013.01); *A61B 1/015* (2013.01); *A61M 2205/581* (2013.01)

(58) Field of Classification Search
CPC ............ A61M 5/3157; A61M 5/14526; A61M 31/00; A61M 5/1452
See application file for complete search history.

(56) References Cited

U.S. PATENT DOCUMENTS 8,974,417 B2  3/2015  Kumura et al.
9,227,020 B2  1/2016  Tang et al.
(Continued)

FOREIGN PATENT DOCUMENTS

WO  2018019881 A1  2/2018

OTHER PUBLICATIONS

Rao et al., ANovel Absorbable Radiopaque Hydrogel Spacer to Separate the Head of the Pancreas and Duodenum n Radiation Therapy for Pancreatic Cancer, International Journal of Radiation Oncology, vol. 99, No. 5, pp. 1111-1120 (2017).
(Continued)

*Primary Examiner* — Bradley J Osinski
(74) *Attorney, Agent, or Firm* — Bookoff McAndrews PLLC (57) ABSTRACT

A medical device may comprise a flexible sheath defining a lumen extending from a proximal end of the sheath to a distal end of the sheath. The sheath may include a piston slidably received within the lumen; an agent disposed in the lumen distal to the piston; and pneumatic fluid disposed in the lumen proximal of the piston. The device may also comprise handle at a proximal end of the sheath, the handle including: a plunger received in a reservoir, wherein the reservoir is in fluid communication with the lumen. The reservoir may contain pneumatic fluid. The handle may also include a gear. An amount of rotation of the gear in a first direction may correspond to an amount that the plunger advances distally in the reservoir to displace pneumatic fluid. The displacement of the pneumatic fluid may advance the piston distally to deliver an amount of agent from the sheath.

20 Claims, 4 Drawing Sheets

(51) Int. Cl.
*A61M 5/145* (2006.01)
*A61M 31/00* (2006.01)

(56) References Cited

U.S. PATENT DOCUMENTS

2005/0070915 A1* 3/2005 Mazzuca ............ A61B 17/8822
  606/92
2009/0264831 A1* 10/2009 Thompson ....... A61B 17/00491
  604/191

OTHER PUBLICATIONS

Kerdsirichairat et al., Hydrogel Spacer for Borderline Resectable and Locally Advanced Pancreatic Cancer: A Feasibility Human Study, Gastroenterology (Aug. 28, 2019) (3 pages).

\* cited by examiner

AGENT DELIVERY DEVICES

CROSS-REFERENCE TO RELATED APPLICATIONS

This application claims the benefit of priority of U.S. Provisional Patent Application No. 62/957,492, filed Jan. 6, 2020, the entirety of which is incorporated herein by reference.

TECHNICAL FIELD

The disclosure relates generally to agent delivery devices. More particularly, embodiments of the disclosure relate to catheter devices for delivering one or more agents endoscopically.

BACKGROUND

Agents may be delivered during medical procedures, such as endoscopic procedures. During an endoscopic procedure, a user inserts a sheath of an endoscope into a body lumen of a patient. The user utilizes a handle of the endoscope to control the endoscope during the procedure. Tools are passed through a working channel of the endoscope via, e.g., a port in the handle, to deliver treatment at the procedure site, near a distal end of the endoscope. The procedure site is remote from the operator.

During an endoscopic procedure, agents may be delivered by a device inserted into the working channel of the endoscope. If an agent is introduced to the device at its proximal end, via the port, some of the agent may be retained within portions of the device within the working channel and may not be delivered to the procedure site. However, a user may desire to deliver an entirety or near an entirety of an agent, without leaving leftover agent in the device. A user may also desire to deliver a controlled volume or dose of the agent. Therefore, a need exists for agent delivery devices.

SUMMARY

Examples of the disclosure relate to, among other things, agent delivery devices. Each of the examples disclosed herein may include one or more of the features described in connection with the disclosed examples.

In one example, a medical device may comprise a flexible sheath defining a lumen extending from a proximal end of the sheath to a distal end of the sheath. The sheath may include a piston slidably received within the lumen; an agent disposed in the lumen distal to the piston; and pneumatic fluid disposed in the lumen proximal of the piston. The device may also comprise handle at a proximal end of the sheath, the handle including: a plunger received in a reservoir, wherein the reservoir is in fluid communication with the lumen. The reservoir may contain pneumatic fluid. The handle may also include a gear. An amount of rotation of the gear in a first direction may correspond to an amount that the plunger advances distally in the reservoir to displace pneumatic fluid. The displacement of the pneumatic fluid may advance the piston distally to deliver an amount of agent from the sheath.

Any of the devices described herein may have any of the following features. The gear may be fixed to a rotatable shaft. A first nut may be received within a cavity of the shaft and is fixed with respect to the shaft. The plunger may be received in a central opening of the first nut. The first nut may have features configured to engage with features of the plunger. The handle may include a second nut that is fixed with respect to the handle. The plunger may be received in a central opening of the second nut. The second nut may have features configured to engage with the features of the plunger. The shaft and the gear may be rotatable via at least one of a knob or a lever. The shaft may be a first shaft. The device may further comprise: a second shaft. Movement of the second shaft along a longitudinal axis of the second shaft in a second direction may cause an end of the second shaft to exert a force on a tooth of the gear, causing rotation of the gear. A spring may be disposed about the second shaft, such that movement of the shaft in the second direction compresses the spring. The gear may be a ratcheted gear that provides tactile or auditory feedback regarding the amount of agent delivered. The plunger may be connected to a rack gear that extends approximately parallel to the plunger. The gear of the handle may engage with the rack gear. The ratcheted gear may be fixed to a wheel that is configured to be contacted by a user. Rotation of the wheel may cause rotation of the ratcheted gear. The rotation of the ratcheted gear may cause movement of the rack gear in a distal direction along a longitudinal axis of the rack gear. The movement of the rack gear in the distal direction may cause movement of the plunger in the distal direction. The plunger may be connected to the rack gear via a bridge. The bridge may be contactable by a user such that a user may contact the bridge to advance the plunger in the distal direction. The ratcheted gear may be movable only in the first direction. The sheath may further include a needle extending from the distal end of the sheath. The needle may be retractable.

In another example, a medical device may comprise: a flexible sheath defining a lumen extending from a proximal end of the sheath to a distal end of the sheath. The sheath may include: a piston slidably received within the lumen; an agent disposed in the lumen distal to the piston; and pneumatic fluid disposed in the lumen proximal of the piston. The device may also include a handle. The handle may include a gear. The rotation of the gear may cause displacement of the pneumatic fluid in a distal direction, advancing the piston distally to deliver an amount of agent from the sheath. The handle may also include a ratchet lock configured to engage with the gear and to provide feedback to a user. The gear may be rotatable by at least one of: a rotatable knob fixed to the gear; or a shaft configured to be advanced in a first direction along a longitudinal direction of the shaft to exert a force on a tooth of the gear. The gear may be a circular gear. The circular gear may be configured to interact with a rack gear. The rack gear may be fixed to a plunger extending approximately parallel to the rack gear.

An example medical method may comprise: inserting a flexible sheath into a body lumen of a patient. The flexible sheath may define a lumen extending from a proximal end of the sheath to a distal end of the sheath. The sheath may include: a piston slidably received within the lumen; an agent disposed in the lumen distal to the piston; and pneumatic fluid disposed in the lumen proximal of the piston. The method may further include activating an actuator to displace the pneumatic fluid and deliver the agent from the sheath; receiving auditory or tactile feedback from a ratcheted gear of the actuator; and ceasing activation of the actuator when a predetermined amount of the agent has been delivered.

Any of the example methods or devices disclosed herein may include any of the following features. The auditory or tactile feedback may indicate an amount of the agent delivered from the sheath.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

An agent delivery device may be configured to house an agent at a distal end of the delivery device so that, after the agent is deployed to a treatment site, an amount of agent remaining within the delivery device is minimal and waste of the agent is avoided. The agent delivery device may facilitate delivery of agents in gel form (e.g., hydrogels). Housing the agent at the distal end of the device may facilitate delivery of gels by not requiring that the gel be passed through the length of the delivery device. Various actuation mechanisms may be utilized in order to actuate the delivery device to deliver the agent. These mechanisms may include ratcheted gears that facilitate administration of a known amount of agent.

Figure 1:
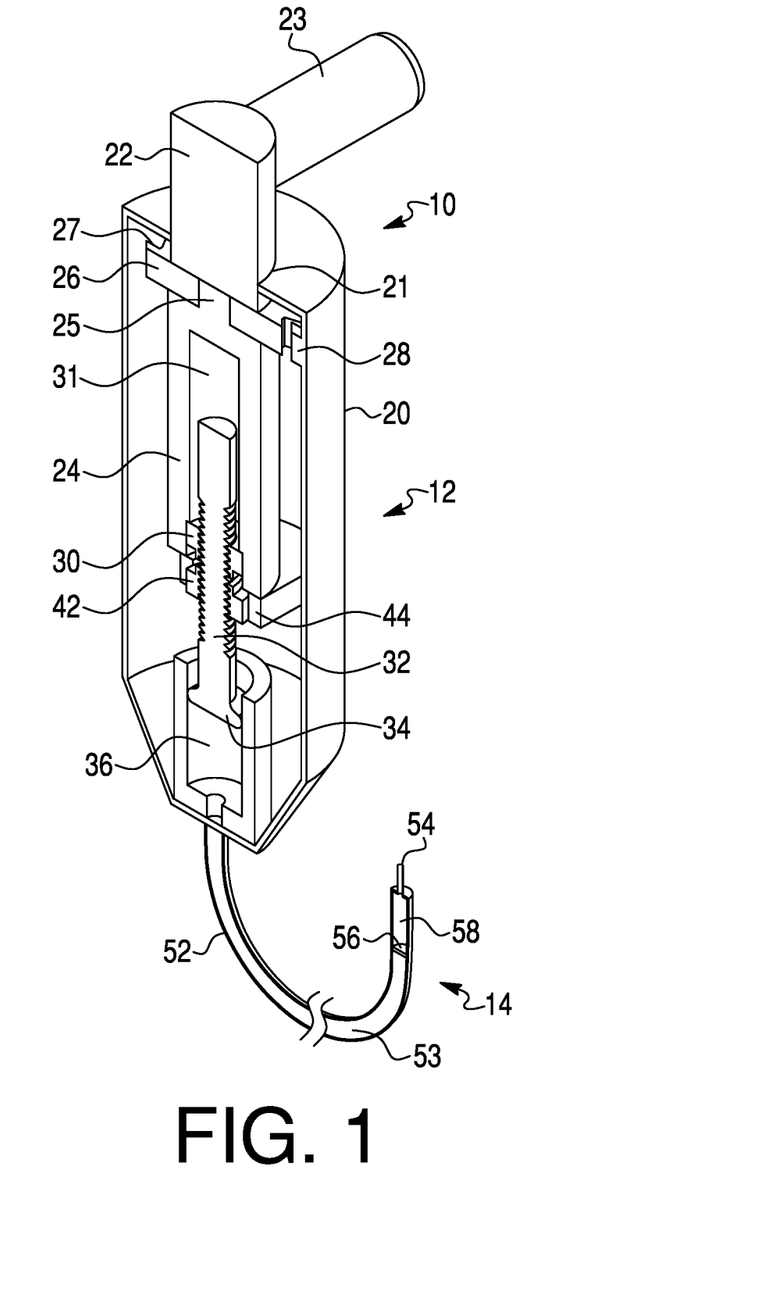
FIG. 1 shows a cross-sectional view of a first delivery device.

FIG. 1 shows an exemplary delivery device 10. Delivery device 10 may include a handle 12 (e.g., an operation portion) and an insertion portion 14. Delivery device 10 may be configured for use with an endoscope (not shown). Although the term endoscope may be used herein, it will be appreciated that other devices, including, but not limited to, duodenoscopes, colonoscopes, ureteroscopes, bronchoscopes, laparoscopes, sheaths, or any other suitable delivery device may be used. For example, insertion portion 14 may be inserted into a working channel of an endoscope via, for example, a port in the endoscope. Handle 12 may remain proximal to the port, outside of the working channel. The endoscope may be inserted into a body lumen of a patient, either before or after insertion of insertion portion 14 into the working channel. Insertion portion 14 may be navigated through a body lumen to a treatment site via the endoscope. Alternatively, delivery device 10 may be used without an endoscope. In such examples, insertion portion 14 may be inserted into a body lumen of a patient or may otherwise be introduced to a body of a patient. Handle 12 may remain external to the patient so that it may be manipulated by a user.

Handle 12 may include a housing 20. Housing 20 may have a generally cylindrical shape and may have a tapered distal end. Housing 20 may have a cavity formed therein for receiving components of handle 20, including the actuator described herein. Housing 20 may have an opening 21 formed in a proximal end of housing 20. A handle or knob 22 may be received within opening 21. Opening 21 and a knob 22 may be sized so that knob 22 is rotatably movable within opening 21, about an axis of knob 22. The axis of knob 22 about which knob 22 is rotatable may be parallel or coaxial with a longitudinal axis of housing 20. Housing 20 may prevent movement of knob 22 that is not rotation about the axis of knob 22 (e.g., a size of opening 21 may prevent knob 22 from substantial radial movement, such as wobbling of knob 22). Knob 22 may include a levered arm 23 that extends perpendicularly or approximately perpendicularly from the axis of knob 22. Arm 23 (or knob 22) may be configured to be contacted by a user (e.g., by the fingers of a user). Force exerted on arm 23 in a direction perpendicular to a longitudinal axis of arm 23 may provide a rotational torque on knob 22, causing knob 22 to rotate about the axis of knob 22. Arm 23 is merely an exemplary structure for facilitating rotational movement of knob 22, and other structures may be used (e.g., knob 22 may be directly contacted by a user). Knob 22 may be connected to or formed integrally with a shaft 24. Rotation of knob 22 may cause corresponding rotation of shaft 24 about a longitudinal axis of shaft 24.

A gear 26 may be disposed circumferentially about shaft 24 and/or knob 22. Shaft 24 may have a neck portion 25 that has a smaller diameter than a remainder of shaft 24. Gear 26 may be disposed about neck 25. Gear 26 may have teeth 27 formed on a circumferential edge thereof. Knob 22, shaft 24, and gear 26 may be fixed with respect to one another via any suitable mechanism (e.g., adhesive, locks, snap-fit, etc). Although knob 22, shaft 24, and gear 26 are shown as separate components, they may be formed integrally from one piece of material via, e.g., molding. FIG. 1 shows gear 26 as being located near a proximal end of shaft 24. However, it will be appreciated that gear 26 may alternatively be located at other portions of shaft 24 (e.g., a middle portion of shaft 24 or near a distal portion of shaft 24).

An inner surface of housing 20 may define a ratchet lock 28. Alternatively, a ratchet lock 28 may be a separate element that is attached to an inner surface of housing 20. Ratchet lock 28 may be sized and shaped to interact with teeth 27 of gear 26, so that gear 26 is a ratcheted gear, in the following manner. Ratchet lock 28 may allow rotation of gear 26 and, thus, shaft 24 in only one direction. Furthermore, ratchet lock 28 may provide tactile and/or auditory feedback to a user, as described in further detail below.

A rotating nut 30 may be received in a cavity 31 of shaft 24. Rotating nut 30 may be fixed relative to shaft 24 such that rotation of shaft 24 causes rotation of rotating nut 30. Rotating nut 30 may be formed of any suitable material, including metal or plastic. Rotating nut 30 may be a separate component from shaft 24 or may be formed integrally from the same material as shaft 24 as one, single, piece. Rotating nut 30 may be fixed to shaft 24 so that it may not move in a proximal or distal direction.

A plunger 32 may be received within an opening of rotating nut 30. Plunger 32 may have a longitudinal axis that is parallel to or coaxial with the longitudinal axis of shaft 24. An inner surface of rotating nut 30 and an outer surface of plunger 32 may have complementary features, such as threads, helical ridges, helical grooves, or other features formed thereon. Plunger 32 may have functionality of a lead screw. Plunger 32 may include a distal end 34. As shown in FIG. 1, distal end 34 may have a larger cross-sectional size than more proximal portions of plunger 32. Alternatively, plunger 32 may have a uniform cross-sectional size, or a cross-sectional size of plunger 32 may vary in other manners.

Distal end 34 of plunger may be received in a reservoir 36. Reservoir 36 may be formed integrally from a wall of housing 20 or may be a separate component fixed to housing 20. Reservoir 20 may have an open proximal end, in which distal end 34 is received. Reservoir 20 may also be in fluid communication with a lumen 53 of sheath 52 (discussed in further detail below), via an opening in a distal end of reservoir 20. Reservoir 20 may receive a pneumatic fluid. The pneumatic fluid may be incompressible or may be compressible. The pneumatic fluid may include any suitable pneumatic fluid. For example, the pneumatic fluid may be bio-compatible and may include saline solution or water. An outer surface of distal end 34 of plunger 32 may form a seal with an inner surface of reservoir 36, such that the pneumatic fluid may not move proximally past distal end 34. Further details of the pneumatic fluid and its functionality will be discussed in further detail below.

A fixed nut 42 may be received in a nut receptacle 44. Nut receptacle 44 may be defined by walls of housing 20 or may be a separate component from housing 20. Nut receptacle 20 may be disposed distal to a distal end of shaft 24. Fixed nut 42 may be fixed with respect to housing 20. Fixed nut 42 may have any of the relevant properties of rotating nut 30, including threads or other features formed on an inner surface thereof, which may or otherwise interact with features (e.g., threads) of plunger 32.

When a force is exerted on arm 23, or knob 22 is otherwise rotated (in a direction permitted by ratchet lock 28), such rotation may be transmitted to shaft 24 and gear 28. Rotating nut 30 may rotate along with shaft 24, causing threads or other features of rotating nut 30 to interact with threads or other features of plunger 30, and causing plunger 32 to rotate. Because fixed nut 42 (which also has threads or other features) does not rotate, the rotational motion of shaft 24 may result in longitudinal movement of plunger 34 along its longitudinal axis in a distal direction because plunger 30 is not permitted to spin freely, along with rotating nut 30. Absent fixed nut 42, plunger 30 may rotate along with rotating nut 30 and not move longitudinally. Thus, rotational motion of knob 22 is converted to longitudinal, distal movement of plunger 34.

Due to ratchet lock 28, the rotational movement of shaft 24 and rotating nut 30 may only be in one direction, which causes distal movement of plunger 34. Ratchet lock 28 may prevent rotation in the opposite direction, which would, absent ratchet lock 28, cause proximal movement of plunger 34. Further details regarding the effects of the distal movement of plunger 34 will be discussed below.

Insertion portion 14 may include a sheath (e.g., a catheter) 52 and a needle 54. Insertion portion 14 may have any of the features of the devices disclosed in U.S. Provisional Patent Application No. 62/942,887, filed Dec. 3, 2019, which is hereby incorporated by reference in its entirety. A cross-sectional diameter of sheath 52 may be such that sheath 52 can be advanced through a working channel of an endoscope. Sheath 52 may be formed of flexible material, facilitating advancement of sheath 52 through a body lumen of a patient. A lumen 53 may extend from a proximal portion of sheath 52 to a distal portion of sheath 52. Although one lumen 53 is shown, it will be appreciated that multiple lumens may extend through sheath 52.

Needle 54 may be sharp at its distal end so that it may pierce body tissue, or needle 54 may be dull. Needle 54 may be formed of a rigid material (e.g., metal or rigid plastic) or may be formed of a flexible material. Needle 54 and sheath 52 may be made of the same materials or of different materials. Needle 54 and sheath 52 may be formed of a single, integral structure or may be formed of separate components and attached to one another by any suitable technique known in the art. Needle 54 may be fixed relative to sheath 52 or may be movable (e.g., retractable and extendable). Needle 54 may be sheathed or shielded to permit needle 54 to pass through a working channel of an endoscope without damaging needle 54 or the endoscope. Sheath 52 may have a blunt distal end, to which needle 54 may be affixed (as shown in FIG. 1). Alternatively, sheath 52 may taper toward needle 54.

A piston or diaphragm 56 may be slidably disposed near a distal end of sheath 52. Piston 56 may be sized and shaped to mate with an inner surface of lumen 53. Piston 56 may include material that forms a seal with a surface of lumen 53. A portion of lumen 53 distal to piston 56 may form a chamber 58. An agent may be received within chamber 58. The agent may be a gel, liquid, powder, etc. For example, the agent may include a hydrogel, a spacer gel, a hemostatic agent, a clotting agent, a drug or other medicament, etc. The agent may come preloaded in chamber 58. Chamber 58 may also be configured to store separate components (e.g., two components) of an agent that are combined when the agent is dispensed. For example, chamber 58 may include one or more sub-chambers. Where the agent is preloaded, delivery device 10 or portions of delivery device 10 may be single-use. Alternatively, a user may load the agent into chamber 58 by any suitable means. Sheath 52 may include markings or other indicators of how much of the agent has been loaded into or dispensed from chamber 58. Chamber 58 may be removably attached to a remainder of sheath 52 (e.g., via threads, snap-fit, or other mechanisms) such that a chamber 58 pre-loaded with the agent may be attached to a re-usable (or disposable) portion of sheath 52. After the agent has been dispensed, as described below, chamber 58 may be replaced with a new, preloaded chamber 58.

Lumen 53 may be in fluid communication with reservoir 36, via, e.g., a distal opening of housing 20 and a proximal opening of sheath 52. The pneumatic fluid may be received within reservoir 36, distal to a distalmost face of distal end 34 of plunger 32, and in lumen 53, proximal to piston 56. The pneumatic fluid may have a volume between plunger 32 and piston 56, which may be constant if the pneumatic fluid is not compressible.

In operation, distal end 34 of plunger 32 may initially be located near a proximal end of reservoir 36. Knob 22 may be rotated to cause distal motion of distal end 34 of plunger 32, as described above. The distal motion of distal end 34 may exert a force on the pneumatic fluid in reservoir 36 (and lumen 53), pushing the pneumatic fluid distally. The force from the pneumatic fluid may cause piston 56 to move distally. The distal movement of piston 56 may exert a force on the agent in chamber 58, pushing an amount of agent out of needle 54 that corresponds with an amount of movement of piston 56.

Prior to rotation of knob 22, distal end 34 of plunger 32 may be in a first position. After rotation of knob 22, distal end 34 may be in a second position. A longitudinal distance between the first position and the second position may be multiplied by a cross-sectional area of reservoir 36 to determine a change in the volume of reservoir 36 that may be occupied by the pneumatic fluid. If the pneumatic fluid is non-compressible, the volume of pneumatic fluid displaced by the movement of plunger 32 may be the same as the change in volume of the occupied space of the reservoir 36. This amount of volume of pneumatic fluid that is displaced from reservoir 36 may be equal to a volume of agent that is dispensed from needle 54, if the agent is not compressible. A given amount of movement of distal end 34 may correspond to dispensing a known amount of agent from needle 54, regardless of whether one or more of the agent or the pneumatic fluid is compressible.

Ratchet lock 28 may interact with gear 26 to provide tactile and/or auditory feedback to a user to indicate an amount of agent that is dispensed from needle 54 (because the amount of rotation of knob 22 relates to the amount that plunger 34 is advanced laterally). For example, a selected or predetermined amount of clicks may correspond to dispensing an amount of agent (e.g., a volume of agent) that may be known to the operator. A dose of agent may correspond to different number of clicks/ratchets for different treatment types. An operator may turn knob 22 a selected or predetermined amount to deliver a known amount of agent. The operator may then administer more agent at the same site (via additional rotation of knob 22) or relocate needle 54 to another site in order to delivery further agent, if desired. The features of device 10 may enable precise dosing of the agent to a desired location.

Due to ratchet lock 28, plunger 32 may not be moved proximally. An inability to move plunger 32 proximally may avoid inadvertent application of suction forces to tissue, delivered agent, or other material in a proximal direction. Due to an inability to reset plunger 32 to its initial position, proximal of its position following delivery of the agent, device 10 may be a single use device. Alternatively, ratchet lock 28 may be omitted. In such situations, alternative mechanisms for providing feedback to an operator regarding dosing amounts may be used. Alternatively, device 10 may have mechanisms for resetting plunger 32 following use.

Because the agent may be received in chamber 58 and need not be within portions of lumen that are proximal to piston 56, device 10 facilitates the avoidance of waste of the agent that would result were the agent required to be introduced from a proximal end of device 10, through an entirety of lumen 53, to needle 54. Device 10 allows dispensing of all or substantially all of agent located in chamber 58, without leaving remaining agent in lumen 53. Because the agent is not required to be introduced from a proximal end of device 10, device 10 facilitates dispensing of gels (e.g., hydrogels), which may be more difficult than other types of agents to introduce from a proximal end of a device.

Prior to rotation of knob 22, the agent may be retained within chamber 58, and not exit needle 54, by various mechanisms. For example, a force of air pressure on the agent may retain the agent within chamber 58. A force of gravity may not overcome the air pressure on the agent, causing the agent to be retained within chamber 58. Alternatively, or additionally, a removable barrier may be disposed at or near a distal end of chamber 58 or opening of needle 54. The barrier may be punctured or otherwise removed when the agent is advanced for delivery from needle 54. Additionally or alternatively, a viscosity of the agent may be sufficiently high that the agent does not pass through needle 54 until knob 22 is rotated.

Figure 2:
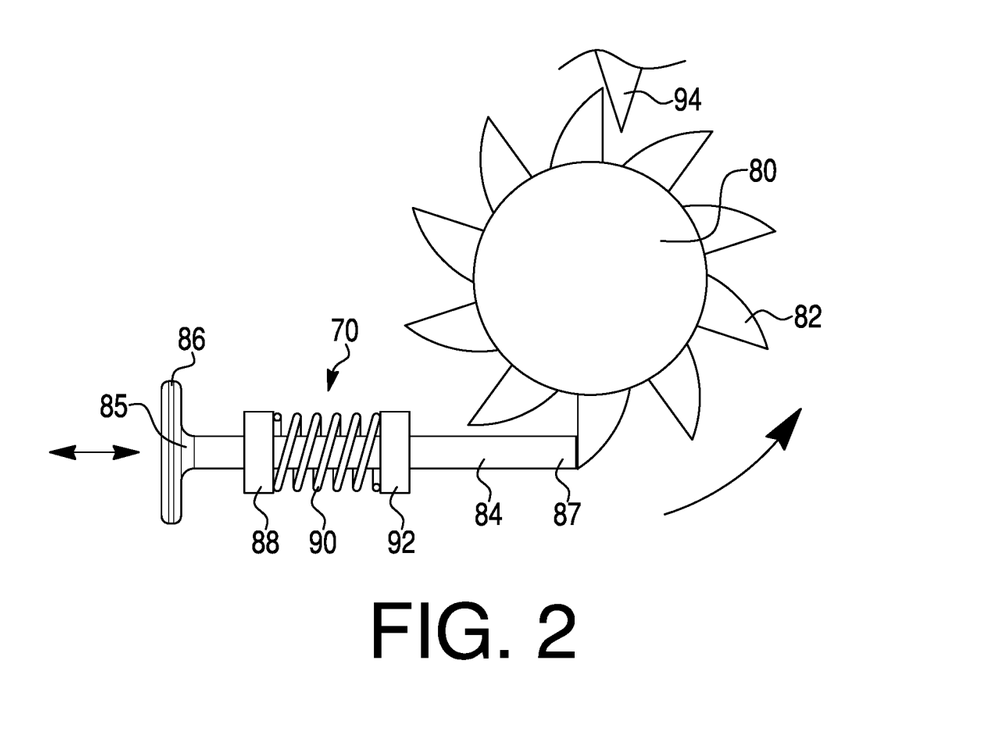
FIG. 2 shows an exemplary, alternative actuation assembly for use with the delivery device of FIG. 1.

FIG. 2 depicts an actuation assembly 70 that may be used as a component of device 10, in an alternative to knob 22 and gear 26. Aspects of device 10 not described with respect to FIG. 2 may be the same as shown in FIG. 1. Actuation assembly 70 may include a gear 80, having teeth 82, and a shaft 84, which may have a longitudinal axis that is perpendicular or otherwise transverse to a rotation axis of gear 80. Gear 80 may have any of the features of gear 26 and may be fixed to shaft 24.

Shaft 84 may terminate in a first end 85 (which extends further in a first direction, to the left in FIG. 2) having a button 86 and a second end 87 (which extends further in a second direction, opposite the first direction, to the right in FIG. 2). Button 86 may be configured to be contacted directly or indirectly by a user. Shaft 84 may have a flange 88 formed thereabout, or another protruding portion. Flange 88 may be formed of the same single, unitary material as shaft 84, or may be a separate component. Flange 88 may be fixed relative to shaft 84. Flange 88 may be fixed to or otherwise contact a first end of a spring 90. A second end of spring 90 may be fixed to or otherwise contact a stop 92. Stop 92 may be fixed relative to a component such as housing 20, and shaft 84 may be movable relative to stop 92. Stop 92 may include a channel within which shaft 84 is movably received.

A ratchet lock 94 may permit rotation of gear 80 in only one direction (i.e., counterclockwise, as shown in FIG. 2), such that gear 80 is a ratcheted gear. Ratchet lock 94 may also provide tactile or auditory feedback (e.g., clicks) to a user as gear 80 rotates, as discussed in further detail below.

In use, shaft 84 may have a first configuration. Spring 90 may be at a relaxed, natural length in the first configuration. Second end 87 may or may not contact one of teeth 82 in the first configuration. To administer a dose of the agent, a user may contact button 86 to exert a force and move button 86 in the second direction (to the right). The second end 87 may begin or continue to contact one of teeth 82 and may exert a force on the one of teeth 82 as second end 87 moves in the second direction. The force on the one of teeth 82 in the second direction (to the right) may cause gear 80 to rotate (in the counter-clockwise direction, as shown in FIG. 2). Meanwhile, one or more of teeth 82 may engage with and pass ratchet lock 94, providing tactile feedback (e.g., clicks) corresponding to a number of teeth 82 that engage with ratchet lock 94.

As explained with respect to ratchet lock 28, a selected or predetermined amount of clicks of ratchet lock 94 may correspond to dispensing an amount of agent (e.g., a volume of agent) that may be known to the operator. A dose of agent may correspond to different number of clicks/ratchets for different treatment types.

As shaft 84 moves in the second direction, flange 88 may exert a compressing force on spring 90. Spring 90 may compress against stop 92. Eventually, spring 90 may compress sufficiently so that shaft 84 may no longer move in the second direction, and shaft 84 may be in a second configuration. A user may then release button 86, and spring 90 may return to its natural, relaxed length so that shaft 84 returns to the first configuration. A user may again contact button 86 to move shaft 84 in the second direction. The steps above may repeat, as shaft 84 contacts another of teeth 82 to deliver further agent.

Rotation of gear 80, which may be effected as explained above, may cause rotation of shaft 24. Agent may be delivered from needle 54, as described above, with respect to FIG. 1. Each time shaft 84 is transitioned between the first and second configuration, a known amount of agent may be delivered. A user may also deliver an amount of agent that is less than the amount delivered by fully advancing shaft 84 in the second direction until spring 90 is fully depressed. A user may determine how far to press button 86 and advance shaft 84 based on a number of clicks felt/heard due to interactions between teeth 82 and ratchet lock 94. An operator may depress button 86 to deliver a known amount of agent. The operator may then administer more agent at the same site (via additional depression of button 86 or additional complete strokes of shaft 84, in which shaft 84 is transitioned from the first configuration to the second configuration) or relocate needle 54 to another site in order to delivery further agent, if desired. The features of device 10 may enable precise dosing of the agent to a desired location.

As described with respect to FIG. 1, because ratchet lock 94 allows rotation only in a single direction (counterclockwise in the FIG. 2, as shown by the arrow near gear 80), actuation assembly 70 may be suited for use with a single-use device 10. Ratchet lock 94 may be omitted and/or a mechanism may allow resetting of plunger 32 so that actuation assembly 70 is usable with a reusable delivery device.

Figure 3A:
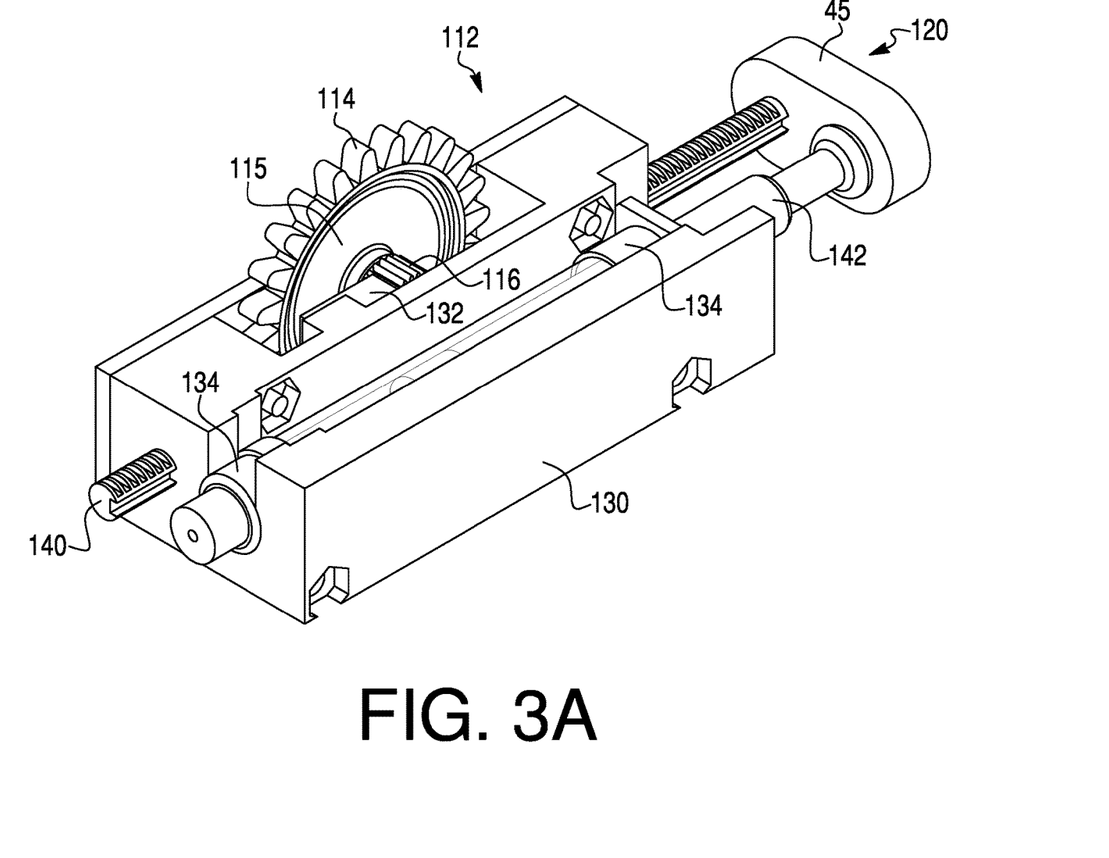
FIGS. 3A and 3B show another actuation assembly.
Figure 3B:
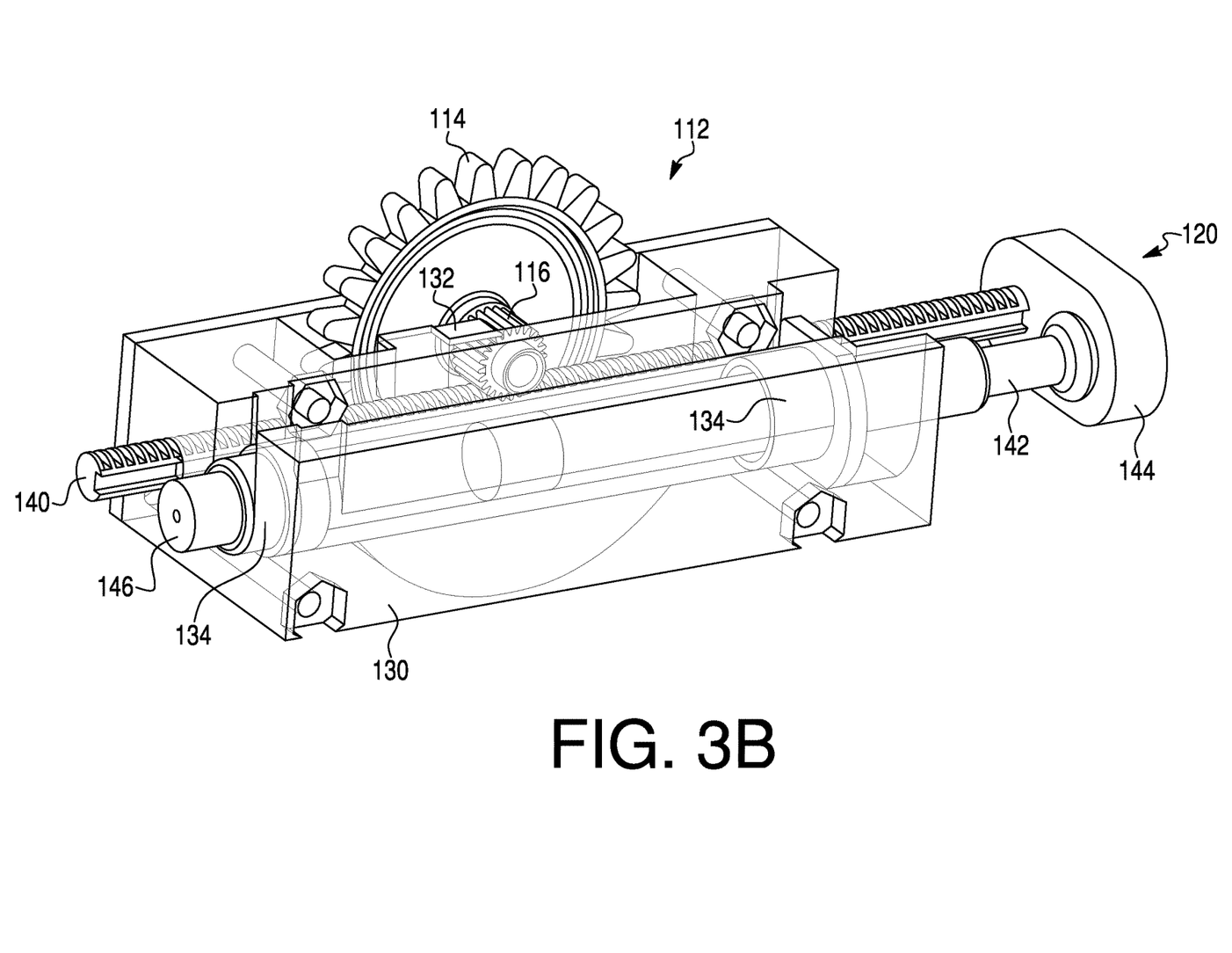

FIGS. 3A and 3B show an actuation assembly 112. FIG. 3A shows a perspective view of actuation assembly 112, and FIG. 3B shows a view where a body 130 of actuation assembly 112 is transparent. Actuation assembly 112 may be used along with insertion portion 14 and reservoir 36 of FIG. 1.

Actuation assembly 112 includes a wheel 114. Wheel 114 may be, for example, a thumb wheel. Wheel 114 may be contacted and rotated by a user (e.g., by a finger or a thumb of a user). Wheel 114 may be rotatable about a central axis perpendicular to a plane of wheel 114. Wheel 114 may have two faces 115, on either side of wheel 114. Faces 115 may be approximately planar. Wheel 114 may include rounded teeth on a circumference thereof. The rounded teeth may be configured to create traction/friction with a finger or thumb of a user, to facilitate a user's ability to rotate wheel 114.

Wheel 114 may be fixed to a circular gear 116. Circular gear 116 may protrude from one of faces 115. A central axis of circular gear 116 may be coaxial with the central axis of wheel 114. Wheel 114 and circular gear 116 may be formed of a single, unitary piece of material. Alternatively, wheel 114 and circular gear 116 may be separate components that are fixed relative to one another by any suitable means. A side of circular gear 116 may be directly fixed to one of faces 115, or circular gear 116 and wheel 114 may each be fixed relative to a shared axle. Circular gear 116 may have a smaller radius than wheel 114. Circular gear 116 may include teeth around a circumference thereof. The teeth of circular gear 116 may extend in a direction parallel to the central axis of circular gear 116 and wheel 114.

At least portions of wheel 114 and gear 116 may be received within a body 130. Body 130 may have any of the properties of housing 20, described above. A portion of wheel 114 may emerge from body 130 (e.g., via an opening formed in body 130), such that it may be contacted by a user. Body 130 may define a ratchet lock 132. Alternatively, ratchet lock 132 may be formed of a separate piece of material and attached to body 130 or another component. Ratchet lock 132 may be configured to interact with teeth of gear 116, such that gear 116 is a ratcheted gear. Ratchet lock 132 may allow rotation of gear 116 (and, therefore, wheel 114) only in one direction.

A plunger assembly 120 may include a rack gear 140 and a plunger 142, connected at their proximal ends via a bridge portion 144. Rack gear 140 may have a longitudinal axis that is parallel to or approximately parallel to a longitudinal axis of plunger 142. Rack gear 140 and plunger 142 may be at least partially movably received within body 130 (e.g., within channel(s) of body 130). Body 130 may include guides 134, which may be, for example, annular rings. Guides 134 may maintain plunger 142 in a desired position, such that plunger 142 extends parallel to rack gear 140 and such that plunger 142 may only be moved longitudinally, limiting radial wobble of plunger 142.

Circular gear 116 may be positioned such that teeth of circular gear 116 interact with teeth of rack gear 140. Rack gear 140 may have teeth that are shaped and sized to be complementary to a shape and size of teeth of circular gear 116. Teeth of rack gear 140 may extend perpendicularly to a longitudinal axis of rack gear 140. When a user exerts a force on a first side of wheel 114 in a proximal direction, a side of circular gear 116 that is opposite (e.g., diametrically opposite) the first side of wheel 114 may engage with rack gear 140 to move rack gear distally. Movement of rack gear 140 in a distal direction may cause bridge 144 to move distally, thereby causing plunger 142 to move distally along a longitudinal axis of plunger 142. Rotational movement of wheel 114 may be converted to linear, longitudinal movement of plunger 142. Ratchet lock 132 may prevent rotation of rack gear 140 in the opposite direction from that described above, thereby preventing movement of rack gear and plunger in a proximal direction. A user may be able to rotate wheel 114 in only one direction.

A distal end 146 of plunger 142 may be received in a structure such as reservoir 36. Distal end 146 may have the shape shown in FIG. 3B or may include a portion with a larger cross-sectional area, such as distal end 34 of plunger 32. Distal end 146 may form a seal with a structure such as reservoir 36, such that the pneumatic fluid received in reservoir 36 may not move proximally of distal end 146.

Bridge portion 144 may be received within body 130 or may be external to body 130. Another housing (not shown) may encompass all or portions of actuation assembly 112 shown in FIGS. 3A and 3B, including bridge portion 144. Alternatively, bridge portion 144 may be external to body 130 or to any housing.

In operation, a user may contact wheel 114 and rotate wheel 114, thereby rotating gear 116. Rotation of circular gear 116 may cause distal movement of rack gear 140 and plunger 142, as described above. Plunger 142 may exert a force on pneumatic fluid received in reservoir 36, thereby causing piston 56 to move distally, expelling agent from chamber 58 and needle 54, as described above. Circular gear 116 may engage with ratchet lock 132. Interactions between circular gear 116 and ratchet lock 132 may provide tactile and/or auditory feedback to a user to indicate an amount of agent that is dispensed from needle 54 (because the amount of rotation of circular gear 132 relates to the amount that plunger 142 is advanced laterally). For example, a selected or predetermined amount of clicks may correspond to dispensing an amount of agent (e.g., a volume of agent) that may be known to the operator. A dose of agent may correspond to different number of clicks/ratchets for different treatment types. An operator may rotate wheel 114 a selected or predetermined amount to deliver a known amount of agent (based, e.g., on a number of clicks). The operator may then administer more agent at the same site (via additional rotation of wheel 114) or relocate needle 54 to another site in order to delivery further agent, if desired. The features of device 10 may enable precise dosing of the agent to a desired location.

Alternatively, where bridge portion 144 is not encompassed by body 130 or a housing, a user may directly contact bridge portion 144 to override the metering functions of wheel 114. For example, a user may directly contact bridge portion 144 to advance piston 142 distally by, e.g., a greater amount than would be achieved by rotation of wheel 114 with the same effort. Depression of bridge portion 144 to move piston 142 distally may cause circular gear 116 to rotate and to engage with ratchet lock 132. Engagement between circular gear 116 and ratchet lock 132 may provide tactile or auditory feedback, as described above. Such feedback may provide information to a user about an amount of agent that is being delivered while the user is contacting and depressing bridge portion 144. A user may administer dosing similarly to the methods described above, when a user contacts wheel 114.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device comprising:
   a flexible sheath defining a lumen extending from a proximal end of the sheath to a distal end of the sheath, and wherein the sheath includes:
   a piston slidably received within the lumen;
   an agent disposed in the lumen distal to the piston; and
   a pneumatic fluid disposed in the lumen proximal of the piston; and
   a handle at a proximal end of the sheath, the handle including:
   a plunger received in a reservoir, wherein the reservoir is in fluid communication with the lumen, and wherein the reservoir contains the pneumatic fluid; and
   a gear, wherein an amount of rotation of the gear in a first direction corresponds to an amount that the plunger advances distally in the reservoir to displace the pneumatic fluid, and wherein the displacement of the pneumatic fluid advances the piston distally to deliver an amount of the agent from the sheath.

2. The medical device of claim 1, wherein the gear is fixed to a rotatable shaft.

3. The medical device of claim 2, wherein a first nut is received within a cavity of the shaft and is fixed with respect to the shaft, wherein the plunger is received in a central opening of the first nut, and wherein the first nut has features configured to engage with features of the plunger.

4. The medical device of claim 3, wherein the handle includes a second nut that is fixed with respect to the handle, wherein the plunger is received in a central opening of the second nut, and wherein the second nut has features configured to engage with the features of the plunger.

5. The medical device of claim 2, wherein the shaft and the gear are rotatable via at least one of a knob or a lever.

6. The medical device of claim 2, wherein the shaft is a first shaft, and further comprising:
   a second shaft, wherein movement of the second shaft along a longitudinal axis of the second shaft in a second direction causes an end of the second shaft to exert a force on a tooth of the gear, causing rotation of the gear.

7. The medical device of claim 6, wherein a spring is disposed about the second shaft, such that movement of the shaft in the second direction compresses the spring.

8. The medical device of claim 1, wherein the gear is a ratcheted gear that provides tactile or auditory feedback regarding the amount of agent delivered.

9. The medical device of claim 1, wherein the plunger is connected to a rack gear that extends approximately parallel to the plunger, and wherein the gear of the handle engages with the rack gear.

10. The medical device of claim 9, wherein the gear is a ratcheted gear, wherein the ratcheted gear is fixed to a wheel that is configured to be contacted by a user, and wherein rotation of the wheel causes rotation of the ratcheted gear.

11. The medical device of claim 10, wherein the rotation of the ratcheted gear causes movement of the rack gear in a distal direction along a longitudinal axis of the rack gear, and wherein the movement of the rack gear in the distal direction causes movement of the plunger in the distal direction.

12. The medical device of claim 11, wherein the plunger is connected to the rack gear via a bridge, and where the bridge is contactable by a user such that a user may contact the bridge to advance the plunger in the distal direction.

13. The medical device of claim 1, wherein the gear is a ratcheted gear, wherein the ratcheted gear is movable only in the first direction.

14. The medical device of claim 1, wherein the sheath further includes a needle extending from the distal end of the sheath.

15. The medical device of claim 14, wherein the needle is retractable.

16. A medical device comprising:
    a flexible sheath defining a lumen extending from a proximal end of the sheath to a distal end of the sheath, and wherein the sheath includes:
    a piston slidably received within the lumen;
    an agent disposed in the lumen distal to the piston; and
    a pneumatic fluid disposed in the lumen proximal of the piston; and
    a handle, including:
    a gear, wherein rotation of the gear causes displacement of the pneumatic fluid in a distal direction, advancing the piston distally to deliver an amount of the agent from the sheath; and
    a ratchet lock configured to engage with the gear and to provide feedback to a user.

17. The medical device of claim 16, wherein the gear is rotatable by at least one of:
    a rotatable knob fixed to the gear; or
    a shaft configured to be advanced in a first direction along a longitudinal direction of the shaft to exert a force on a tooth of the gear.

18. The medical device of claim 16, wherein the gear is a circular gear, wherein the circular gear is configured to interact with a rack gear, and wherein the rack gear is fixed to a plunger extending approximately parallel to the rack gear.

19. A medical method, comprising:
    inserting a flexible sheath into a body lumen of a patient, wherein the flexible sheath defines a lumen extending from a proximal end of the sheath to a distal end of the sheath, and wherein the sheath includes:
    a piston slidably received within the lumen;
    an agent disposed in the lumen distal to the piston; and
    a pneumatic fluid disposed in the lumen proximal of the piston;
    activating an actuator to displace the pneumatic fluid and deliver the agent from the sheath;
    receiving auditory or tactile feedback from a ratcheted gear of the actuator; and
    ceasing activation of the actuator when a predetermined amount of the agent has been delivered.

20. The medical method of claim 19, wherein the auditory or tactile feedback indicates an amount of the agent delivered from the sheath.

* * * * *